United States Patent
Henze et al.

(10) Patent No.: US 6,175,408 B1
(45) Date of Patent: Jan. 16, 2001

(54) APPARATUS FOR DETECTING FOREIGN SUBSTANCE IN STRAND-LIKE TEXTILE MATERIAL

(75) Inventors: Herbert Henze, Mönchengladbach; Olav Birlem, Aachen, both of (DE)

(73) Assignee: W. Schlafhorst AG & Co. (DE)

( * ) Notice: Under 35 U.S.C. 154(b), the term of this patent shall be extended for 0 days.

(21) Appl. No.: 09/470,263

(22) Filed: Dec. 22, 1999

(30) Foreign Application Priority Data

Dec. 22, 1998 (DE) ............................................ 198 59 274

(51) Int. Cl.[7] .................................................. G01N 21/00
(52) U.S. Cl. ............................................ 356/238.3; 372/43
(58) Field of Search .............................. 356/238.1, 238.2, 356/238.3, 429, 430, 318; 250/571, 559.29; 362/259; 372/43, 75, 49; 66/132 R

(56) References Cited

U.S. PATENT DOCUMENTS

| | | |
|---|---|---|
| 5,383,017 | 1/1995 | Schlurch . |
| 5,416,593 * | 5/1995 | Vercruysse ............................ 356/429 |
| 5,499,794 | 3/1996 | Aeppli . |
| 5,530,551 | 6/1996 | Cantrall et al. . |
| 5,535,230 * | 7/1996 | Abe ....................................... 362/259 |
| 5,765,399 * | 6/1998 | Huss et al. ........................... 66/132 R |
| 5,959,316 | 9/1999 | Lowery . |
| 5,962,971 | 10/1999 | Chen . |

FOREIGN PATENT DOCUMENTS

| | | |
|---|---|---|
| 683035 A5 | 12/1992 | (CH) . |
| 683293 A5 | 2/1994 | (CH) . |
| 683294 A5 | 2/1994 | (CH) . |
| 683378 A5 | 2/1994 | (CH) . |
| 0 399 945 A2 | 11/1990 | (EP) . |
| 0 572 592 B1 | 12/1991 | (EP) . |
| 0 643 294 A1 | 3/1995 | (EP) . |
| 0 652 432 A1 | 5/1995 | (EP) . |
| WO 98/33061 | 1/1998 | (WO) . |

OTHER PUBLICATIONS

German Search Report dated Sep. 2, 1999.
European Search Report; EP 99 12 3121; dated May 16, 2000.

* cited by examiner

Primary Examiner—Hoa Q. Pham
Assistant Examiner—Sang H. Nguyen
(74) Attorney, Agent, or Firm—Kennedy Covington Lobdell & Hickman L.L.P.

(57) ABSTRACT

An apparatus detects foreign substances in strand-like textile material, such as slivers or yarn, using a white-light LED. The color detection is effected over more than two color support points whereby the detection of foreign substances in the textile material is improved. The apparatus is preferably operated in combination with a yarn cleaner in spinning or bobbin winding machines.

11 Claims, 1 Drawing Sheet

APPARATUS FOR DETECTING FOREIGN SUBSTANCE IN STRAND-LIKE TEXTILE MATERIAL

CROSS REFERENCE TO RELATED APPLICATIONS

This application claims the benefit of German Application DE P 19859274.4 filed Dec. 22, 1998, herein incorporated by reference.

FIELD OF THE INVENTION

The present invention relates to an apparatus for detecting foreign substances in strand-like textile material, such as slivers or yarn.

BACKGROUND OF THE INVENTION

European Patent Disclosure EP 0 643 294 A1 describes the detection of foreign substances in a textile material by illuminating the test product and measuring the light reflected by the test product such that the presence of a foreign substance can be concluded from a change in the reflected light. For detecting foreign substances that are darker than the test product, the test product is projected on a light background on a sensor and, to detect lighter foreign substances, it is projected on a dark background. As lighting elements, light-emitting diodes (conventionally abbreviated "LED") of a certain color, such as green or red, are used. If the light emitted by the light-emitting diode does not suffice to illuminate the textile material adequately at the material speed required, lighting elements are used that emit a higher quantity of light, such as lasers, flash bulbs, or incandescent bulbs. As an alternative provision for amplifying the emitted light, it is disclosed that the number of LEDs can be increased and that a plurality of LEDs of a certain color can be combined into a so-called multichip LED array. The change in the reflected light, from which the presence of a foreign substance is concluded, comprises a change in the total brightness of the reflected light.

However, the apparatus described in European Patent Disclosure EP 0 643 294 A1 has disadvantages. Since LEDs of a certain color, such as green or red, employ a very narrow wavelength range, certain foreign substances may cause no change in brightness, or may not cause a sufficient change in brightness, thus impairing the reliability of foreign substance detection. Lighting elements with a broader light spectrum, such as lasers, flash bulbs or incandescent bulbs, or with a multichip LED array instead of a single LED, require more parts and considerably more structural space. Yet in certain sensors, such as yarn sensors, only a very limited amount of structural space is available. Also, the energy consumption of an incandescent bulb that is used for instance as an alternative to a single LED is markedly higher.

International Patent Disclosure WO 98/33061 describes the use of different colors or wavelengths. Different colors or wavelengths are intended to prevent the inability to detect contaminated foreign bodies in the test product, or the ability to detect them only poorly. From this Patent Disclosure WO 98/33061 A1, it can be learned that the light intensity of a single LED may be unsatisfactory, and thus to amplify the emitted light quantity and hence, to amplify the electro-optical signal, that a plurality of LEDs should be used instead of a single LED. Using many lighting elements, or using lighting elements that emit light at high intensity, such as arc lamps, however, as already noted above, requires additional components and takes up a considerable portion of the only limited available structural space in a yarn sensor. The apparatus described in Patent Disclosure WO 98/33061 A1 employs a measurement of the total brightness of the reflected light.

SUMMARY OF THE INVENTION

It is accordingly an object of the present invention to provide an improved apparatus for detecting foreign substances in strand-like textile material by using suitable means.

Briefly summarized, the present invention provides an apparatus for detecting foreign substances in strand-like textile material basically comprising means for generation of light, means for exposing the material to the light, and means for evaluating the light reflected from the material, wherein the aforestated objective is achieved by embodying the light generation means to includes a light-emitting diode for generating colored monochromatic light and a frequency transformer for converting the spectrum of the emitted light into white light.

A light-emitting diode that generates colored monochromatic light and has a frequency transformer that emits white light is often referred to as a white-emitting single-chip LED, and will hereinafter be identified as a white-light LED for shorthand purposes. The white-light LED emits light at a substantially higher intensity than previously known LEDs. At the same time, this light has a broad emission spectrum. Additional LEDs for amplifying the light can be dispensed with. It is also unnecessary to use arrangements of additional lighting elements that emit light of a different color. Compared with conventional lighting elements with a broad wavelength spectrum, such as incandescent bulbs, the lifetime of a white-light LED is up to 20 times that of an incandescent bulb. The white-light LED requires substantially less structural space than lasers, flash bulbs or incandescent bulbs. The use of a single white-light LED thus avoids measurement errors of the kind that occur when more than one LED is used because of the fading in intensity or so-called aging of the light emitted by a given LED, which proceeds at a different rate for each LED. Aging of a single white-light LED can be compensated in a relatively simple way by means of a compensation device, which regulates the current delivered and keeps the light intensity constant. To that end, the intensity of the light emitted by the white-light LED is monitored by a sensor.

Even LEDs straight from the factory each emit light at a different intensity. To prevent erroneous measurements, LEDs are selected in accordance with light intensity in classes, and only LEDs from the same class of intensity are used together. This kind of complicated selection can be dispensed with, when a white-light LED is used.

The differences that occur in the light upon comparison of a plurality of white-light LEDs are substantially less than in conventional LEDs. This improves the replicability of the measurements when an LED is replaced. In a white-light LED, whose light-generating LED furnishes blue light as the colored monochromatic light, the wave length spectrum of the light emitted approaches the composition of sunlight. Thus, for example, like sunlight a white-light LED produces a pronounced proportion of blue light and it is therefore especially well suited for the assessment of textile material. White-light LEDs emit a very homogeneous light that can be readily used for measuring purposes.

A white-light LED, in which the LED, the frequency transformer and a lens are disposed in a common housing, requires extraordinarily little structural space and can easily be installed and removed, in the individual components are especially well protected against mechanical action and soiling. A frequency transformer of an epoxy resin molding material with luminescent pigments distributed therein can be embodied and positioned simply and in numerous ways.

While natural colors have a widely scattered reflection range, in pigment dyestuffs, the reflection encountered is virtually single-wave radiation. Reliable color detection and reliable measurement are possible only by exposure to light of a quite specific wavelength in each case. The light of an LED of a certain color, and optionally in a so-called two-color LED the light of one additional LED in another certain color, cover the required wavelength spectrum for detecting pigment colors only inadequately. The white-light LED improves the excitation of the reflection radiation for pigment dyestuffs. This broadens the range of use and improves color detection and measurement.

Measuring the difference in intensity of the spectra of red light and green light, of blue light and green light, and of red light and blue light, as is possible with three color support points, allows the detection of any incident deviations in color values and any drift or migration of the color values. At the same time, a total brightness signal can be formed, which is also evaluated in order to ascertain any deviations.

The detected measurement values are examined for characteristics that allow a conclusion to be drawn about the incidence of foreign substances, such as foreign fibers or shell fragments. Foreign fibers are for example differently colored, or they react differently to dyeing agents, or their surface has a different reflection behavior. Color detection over more than two and preferably three color support points allows substantially more accurate measurement and evaluation and results in accurate color resolution and high reliability of the outcome of measurement. Thus even color changes that were heretofore in the tolerance range of fluctuation in the measured values and were therefore not detected as a color detection can now be detected. With the apparatus of the invention, a more-sensitive reaction to fluctuations is possible.

Further features, details and advantages of the invention will be understood and explained in the following disclosure of a preferred embodiment with reference to the accompanying drawings.

DESCRIPTION OF THE PREFERRED EMBODIMENT

Figure 1:
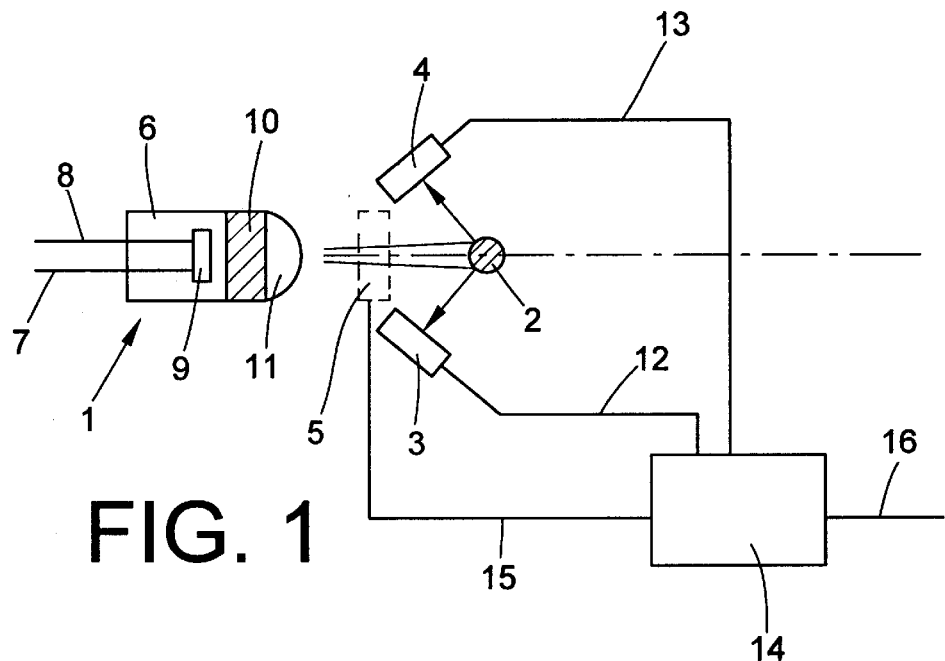
FIG. 1 schematically depicts a measuring apparatus for foreign body detection with a white-light LED, photo sensors, and an evaluation device.

Referring now to the accompanying drawings, the measuring apparatus of FIG. 1 has a white-light LED 1, a yarn 2, and sensors 3, 4, 5 that are embodied as photo sensors. Although the invention is described herein in an embodiment for use with a yarn, it is to be understood by those persons skilled in the art that the invention is equally applicable to any other strand-like or indeterminate length textile material.

The white-light LED 1 comprises a structural unit that has a housing 6, a light-emitting diode 9 embodied as an LED chip and connected to a voltage source, not shown, via the current conductors 7, 8, a frequency transformer 10, and a lens 11. The light-emitting diode, or LED, 9 generates single-colored light, in this exemplary embodiment blue light, which is converted by the frequency transformer 10 and emitted as white light with a broad wavelength spectrum comprising a mixture of blue radiation and yellow converted radiation. The white light is emitted through the lens 11 in the direction of the yarn 2. The frequency transformer 10 comprises an epoxy resin molding material with luminescent pigments distributed therein. The luminescent pigments are adapted in their composition to the light generated by the LED 9.

The light striking the yarn 2 is reflected by the surface of the yarn 2. The sensors 3, 4 detect the reflected light striking them and convert it into a signal proportional to the reflected light intensity, and this signal is delivered over the lines 12, 13 to a signal processing system 14. The signal processing system 14 evaluates the incoming signals based substantially on the measured intensity values. Changes in the intensity of the reflected light, or the exceeding of at least one threshold value, allow the conclusion to be drawn that there are foreign bodies in the yarn 2.

Improved color detection is attained by using a third sensor 5, embodied as a photosensor shown in broken lines in FIG. 1, and is also connected to the signal processing system 14 via the line 15. The sensor 5 is located at a somewhat lower level than the sensors 3, 4, so that it does not impede the course of the beam of light from the white-light LED 1 to the yarn 2. A line 16 serves the purpose of communication between the signal processing system 14 and data processing or other signal processing systems, or serves to control a yarn cleaner, not shown.

Figure 2:
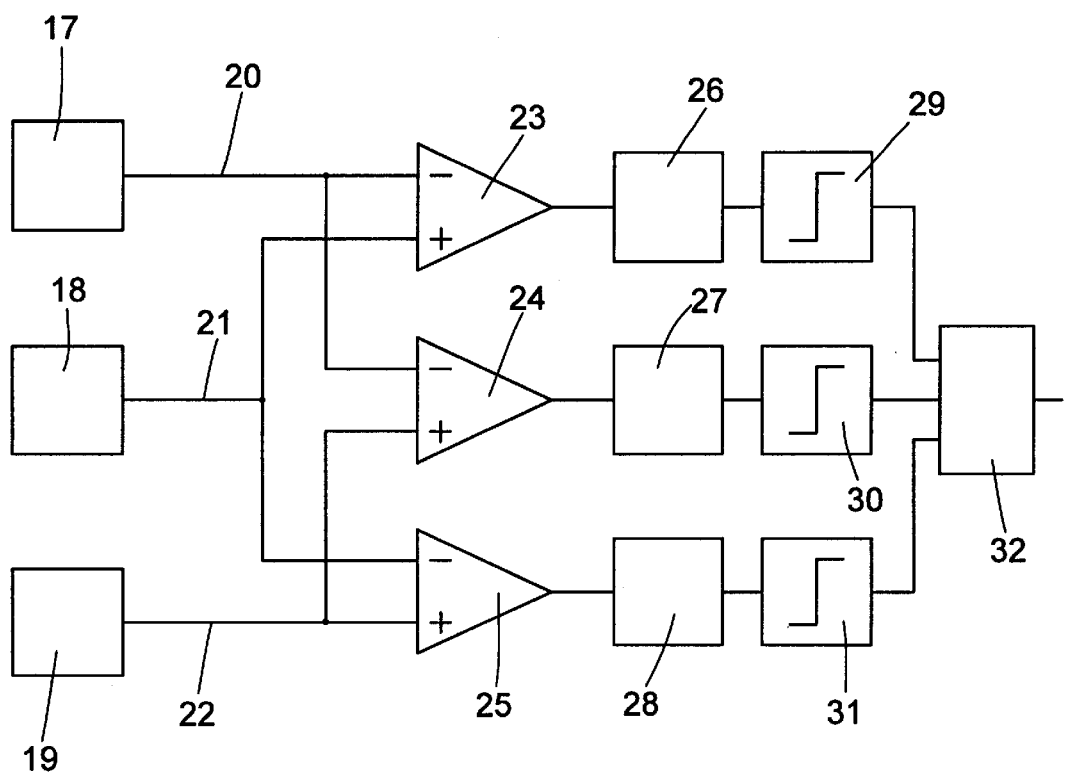
FIG. 2 is a schematic block diagram which illustrates in principle a circuit for evaluating the output of the measurement.

FIG. 2 depicts schematically an exemplary embodiment of a circuit by which the signals of three sensors, identified at 17, 18, 19, having spectral sensitivity in different ranges, are evaluated. In the circuit of FIG. 2, the spectral sensitivity of the sensor 17 is in the red light range, that of the sensor 18 is in the green light range, and that of the sensor 19 is in the blue light range. The sensors 17, 18, 19 are followed by a subtraction stage. The color signal emitted by the respective sensor 17, 18, 19 is delivered over the associated line 20, 21, 22 to the differential signal elements 23, 24, 25, respectively. The sensor 17 communicates with the differential signal elements 23 and 24 via the line 20; the sensor 18 communicates with the differential signal elements 23 and 25 via the line 21; and the sensor 19 communicates with the differential signal elements 24 and 25 via the line 22. The differential signal element 23 receives a color signal from the sensor 17 that is proportional to the intensity of the red light detected, as well as a color signal from the sensor 18 that is proportional to the intensity of the detected green light. The difference in the light intensity of red light and green light is ascertained and carried as a color difference signal to a high-pass filter 26. The high-pass filter 26 passes high-frequency color difference signals and blocks low-frequency color difference signals and thus serves to suppress constant or low-frequency differences.

After passing through the high-pass filter 26, the color difference signal is checked in a comparator 29 for whether a predetermined, adjustable threshold value has been exceeded. If so, an error signal is generated and delivered to a switch element 32.

In substantially similar manner, the differential signal elements 24 and 25 deliver respective color difference signals to respectively associated high-pass filters 27 and 28 which are also connected to respective comparators 30 and 31, whereby the measurement of the difference between the intensity of the color signals of red light and blue light and of blue light and green light is performed simultaneously and in the same way as the measurement of the difference in the intensity of the color signals of red light and green light.

The switch element 32 includes an "OR" circuit and checks whether an error signal is present from the comparator 29, the comparator 30, or the comparator 31. If there is an error signal from at least one comparator 29, 30, 31, a foreign body signal is generated. This finction performed by the switch element 32 is also known as an "OR" operation on the error signals to produce a foreign substance signal. If a foreign substance signal is present, for example through the signal processing system 14 via the line 10, the cutting device of the yarn cleaner is activated, and/or other suitable provisions are initiated for maintaining the desired yarn quantity.

Other details, not explained here, of the design and mode of operation of white-light-emitting single-chip LEDs can be obtained from the article, entitled "Langlebige Beleuchtung mit hohem Wirkungsgrad" [High-Efficiency, Long-Life Lighting], in Components 5/98.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. An apparatus for detecting foreign substances in strand-like textile material, comprising:

(a) a single white-light LED comprising a single light emitting diode that generates colored monochromatic light and a frequency transformer that converts the spectrum of the emitted light from the single light emitting diode into white light including a wide frequency spectrum, (b) a lens located in proximity to said frequency transformer and exposed to the white light that directs the white light towards the strand-like textile material, and (c) a sensor that measures the light reflected from the material.

2. The apparatus of claim 1, wherein the light-emitting diode generates blue colored monochromatic light.

3. The apparatus of claim 1, wherein said lens and said frequency transformer are located in a common housing.

4. The apparatus of claim 1, wherein said frequency transformer comprises a fluorescence agent.

5. The apparatus of claim 1, wherein said frequency transformer comprises an epoxy resin molding material with luminescent pigments distributed therein.

6. The apparatus of claim 1, further comprising additional sensors for measuring the light reflected from the material.

7. The apparatus of claim 6, wherein each of said sensors measures light intensity of a different color.

8. The apparatus of claim 1, further comprising two additional sensors, and wherein said sensors measure, respectively, the intensity of red, green and blue light.

9. A method of detecting foreign substances in strand-like textile material, comprising the steps of illuminating the strand-like textile material only with light generated from a single white-light LED comprising a single light emitting diode that generates colored monochromatic light and a frequency transformer that converts the spectrum of the emitted light from the single light emitting diode into white light including a wide frequency spectrum, and simultaneously measuring the intensity of the light reflected from the strand-like textile material with a sensor arrangement.

10. The method of claim 9, wherein said step of illuminating the strand-like textile material includes directing the light generated from the single white-light LED through a lens disposed in a common housing with the white-light LED.

11. The method of claim 9, wherein said step of measuring the intensity of the reflected light comprises measuring red light intensity with a first sensor, measuring green light intensity with a second sensor, and measuring blue light intensity with a third sensor.

* * * * *